June 13, 1967 G. W. NELSON Plant Pat. 2,748
PLUM TREE
Filed Sept. 17, 1964 2 Sheets-Sheet 1
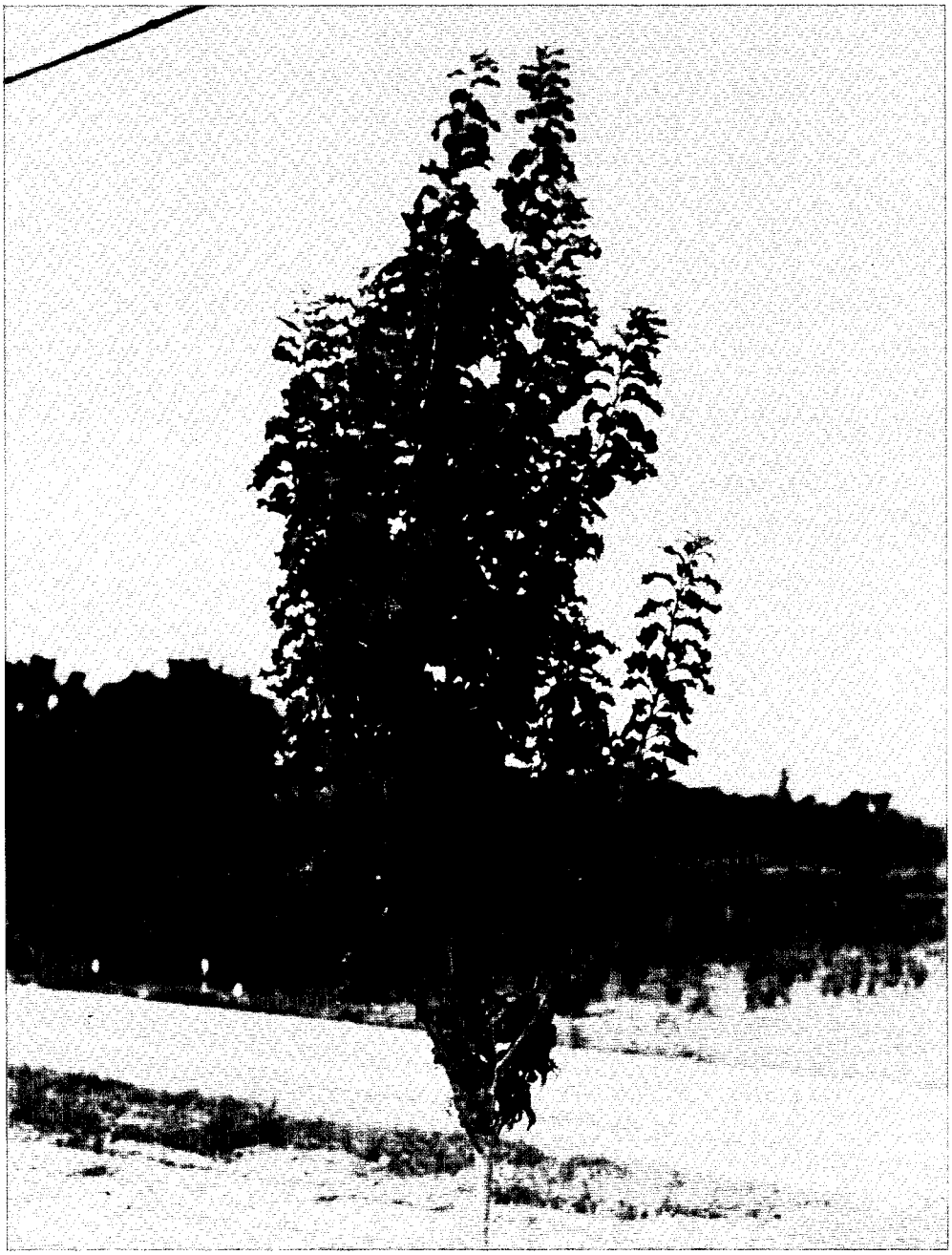
INVENTOR
GEORGE W. NELSON
BY
Adams & Cuayna
ATTORNEYS PLUM TREE
Filed Sept. 17, 1964 2 Sheets-Sheet 2
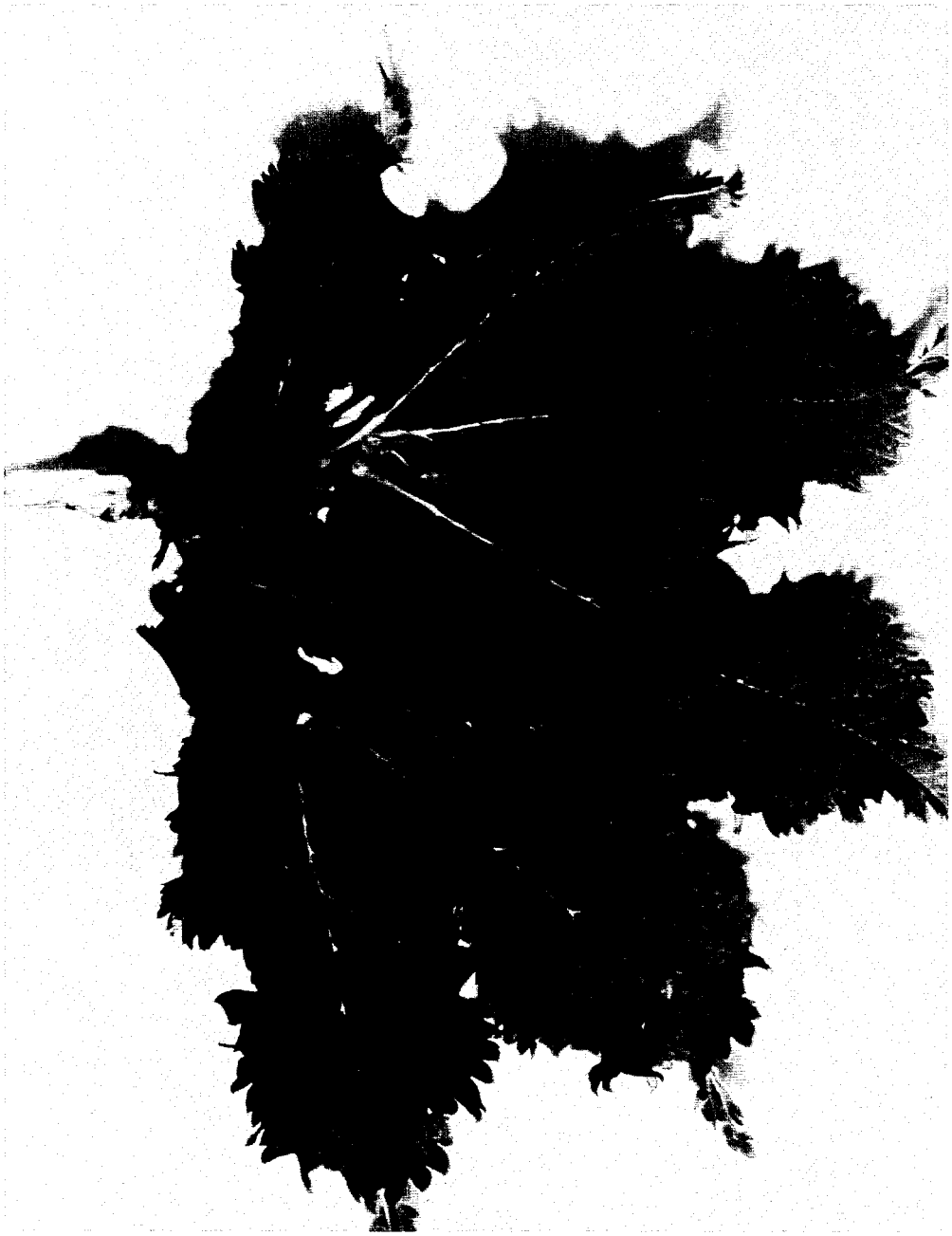
INVENTOR
GEORGE W. NELSON
BY
Adams & Cusayna
ATTORNEYS United States Patent Office Plant Pat. 2,748
Patented June 13, 1967

2,748
PLUM TREE

George W. Nelson, P.O. Box 995,
La Crescent, Minn. 55947

Filed Sept. 17, 1964, Ser. No. 397,351
1 Claim. (Cl. Plt.—38)

My invention relates to a new and distinct variety of plum tree of the genus Prunus which is particularly adapted for ornamental plantings.

This variety was discovered by me as a seedling included in a purchase of nursery stock made from a nursery located near Thief River Falls, Minn. Various plum trees were included in this purchase and all of the plum trees purchased were of the ordinary ornamental plum variety including trees of the Cistena variety in contrast to the plant described herein.

This discovery is, as closely as it is possible to determine, a variety of the genus Prunus, possibly a variety of *Prunus salicina* or a hybrid thereof, sub-genera Prunophora, subfamily Prunoideae of the family Rosaceae.

Because of the unique and distinctive characteristics exhibited by the plant I attempted to asexually reproduce this tree by the budding process on seedling plums in the area around Newport, Minn. This process was not successful. Subsequent to this another attempt to asexually reproduce the plant was attempted in the area of La Crescent, Minn. In this case 3,000 plum seedlings were budded and approximately 95 percent success was attained. It has now been shown that the characteristics of this tree are established and come true through succeeding generations.

Further specimens have also been propagated from the original tree by both the soft wood cuttings and hard wood cuttings processes. In each of the reproduction cases the plant has retained the identity of the parent.

As will be seen from the following description and the accompanying drawings the new variety embodies desirable characteristics not heretofore known.

The accompanying drawings show a mature tree and a portion of a tree limb which particularly illustrates the growth and characteristics of the tree's leaves.

This variety is definitely not a fruit bearer as compared to the ordinary plum. What few fruits have been noted have never matured, reaching only a size of approximately ½ inch to ⅝ inch in diameter and oblate in shape and these fruits have been of no particular merit. A comparison of the fruit colors taken from Matitland Graves, "Color Fundamentals," first edition, McGraw-Hill Book Company, Inc. would be that the skin color compares to 192 FIG. 17–2 YR4 R3.10 and the flesh color of the fruit is shown on page 200, FIG. 17–10 RP4–YR 6.8–8. The ripening time for the fruit in the La Crescent, Minn. area is from approximately September 1st to September 7th. As would be imagined the flowers which do appear on the tree are very infrequent but those that have been noted have been about ⅜ inch to ½ inch in diameter and have been white in color. The blossoms appear in the early part of May.

The variety I have discovered is generally dwarfish in character and may be grown either as a tree or shrub.

Where specimens have had the lower branches pruned out the specimen appears to have attained a maximum height of 10 feet to 12 feet while developing a width of 4 feet to 5 feet and thus provides a compact vertical appearance. The branches of the tree are upright in growth, tending to grow closely to the vertical line of growth thus adding to the compact appearance and in a young tree the foliage bears a close apparance to a petunia plant leaf except for the color. Pruning of the lower branches of the tree tend to give the adult tree a fuller appearance. This is to say that the width of the tree tends to increase slightly.

Leaves are convolute in the bud and evolve out of the bud in a convolute form. As shown, the mature leaves are serrate and crinkled. The upper surfaces of the leaves are distinctively characterized by their lustrous dark green color while the under side of the leaf is grayish green in color. The color of the leaves and foliage taken from the above identified reference book is illustrated on page 196, FIG. 17–6 BG7 B22; from page 197, FIG. 17–7 B3 G3, 2–2; and page 198, FIG. 17–8 PB3 BG# 2–2. These are the closest color descriptions that I have found thus far.

The compact appearance of this variety is further enhanced by the closeness of the leaf nodes which are set apart about ½ inch on the branches. The leaves themselves have a maximum width of approximately 1½ inches and a length of approximately 3½ inches, with an average width of 1 inch and an average length of 2½ inches.

The bark of this variety is purplish brown in color and thus is similar to certain plum varieties and likewise, typical of a plum, the bark is smooth skinned. The bark color is likened to either the Superior plum from the organization of Minnesota Fruit Breeding Farms or the Ember plum from the same organization. Specimens thus far have proved to be particularly hardy and have suffered no ill effects through hard winters. The root system is also similar to the plum family, with the normal main roots and a few rootlets.

The branchlet color taken from the above identified reference book is illustrated on page 197, FIG. 17–7 B8 GY6–8–10 and the dormant twig varies between the colors illustrated on page 200, FIG. 17–10 RP1 YR4–2 and YR3–2. Also the winter buds are characterized by the color illustrated in the same reference book at page 200 RP1 YR4–2.

What is claimed:

A new and distinct variety of plum tree substantially as shown and described herein, particularly characterized by its dwarfish characteristics and the compactness of its growth; its leaves being convolute in the bud and convolute, serrate and crinkled in the mature form with the leaf nodes being closely set on the branches and the leaves being distinctively characterized by their lustrous dark green color; its branches being upright in their growth to present a compact silhouette.

No references cited.

ABRAHAM G. STONE, *Primary Examiner.*
ROBERT E. BAGWILL, *Examiner.*